United States Patent [19]

Bokros

[11] 4,178,639
[45] Dec. 18, 1979

[54] TWO-LEAFLET HEART VALVE

[75] Inventor: Jack C. Bokros, Alpine, Calif.

[73] Assignee: Carbomedics, Inc., San Diego, Calif.

[21] Appl. No.: 894,166

[22] Filed: Apr. 6, 1978

[51] Int. Cl.² ............................................. A61F 1/22
[52] U.S. Cl. .................................... 3/1.5; 137/512.1; 137/527.8
[58] Field of Search ............... 3/1.5, 1; 137/512.1, 137/527, 527.8

[56] References Cited

U.S. PATENT DOCUMENTS

| | | | |
|---|---|---|---|
| 3,448,465 | 6/1969 | Pierce et al. | 3/1.5 |
| 3,579,645 | 5/1971 | Bokros | 3/1.5 |
| 3,835,475 | 9/1974 | Child | 3/1.5 |
| 3,903,548 | 9/1975 | Nakib | 3/1.5 |
| 4,078,268 | 3/1978 | Possis | 3/1.5 |

FOREIGN PATENT DOCUMENTS 1160008  7/1969  United Kingdom ..................... 3/1.5

Primary Examiner—Ronald L. Frinks
Attorney, Agent, or Firm—Fitch, Even & Tabin

[57] ABSTRACT

A heart valve prosthesis has an annular valve body with a central circular passageway and a pair of valve leaflets supported for pivotal movement between closed and open positions. Guides formed with spheroidal surfaces project in opposite directions along the pivotal axis of each leaflet and are received in spheroidal depressions in a pair of upstanding, diametrically opposite supports. The supports are formed with stops outside of the depressions which contact the distal surface of the leaflets at a region apart from the spheroidal guides and determine the open position.

8 Claims, 12 Drawing Figures

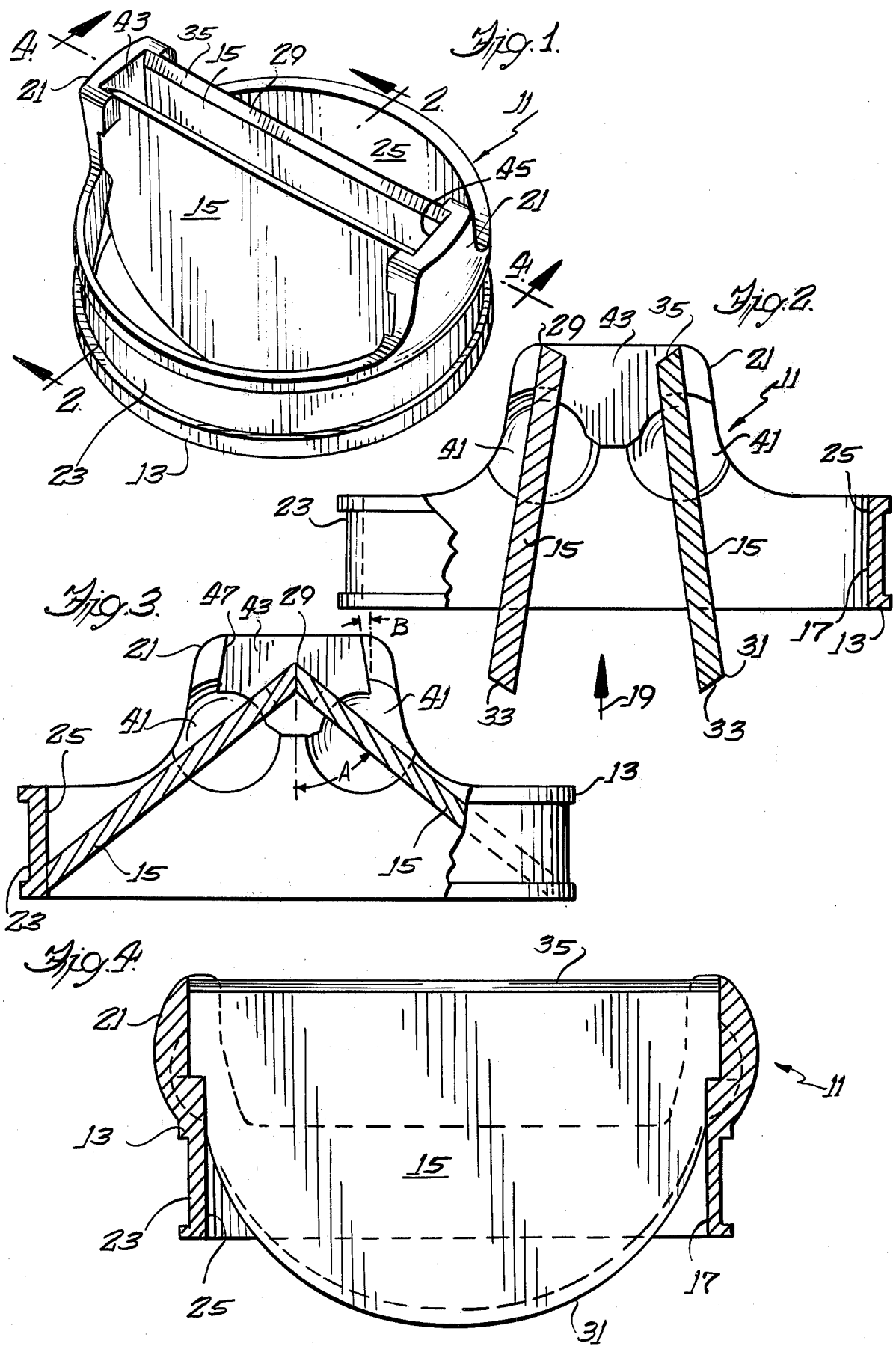

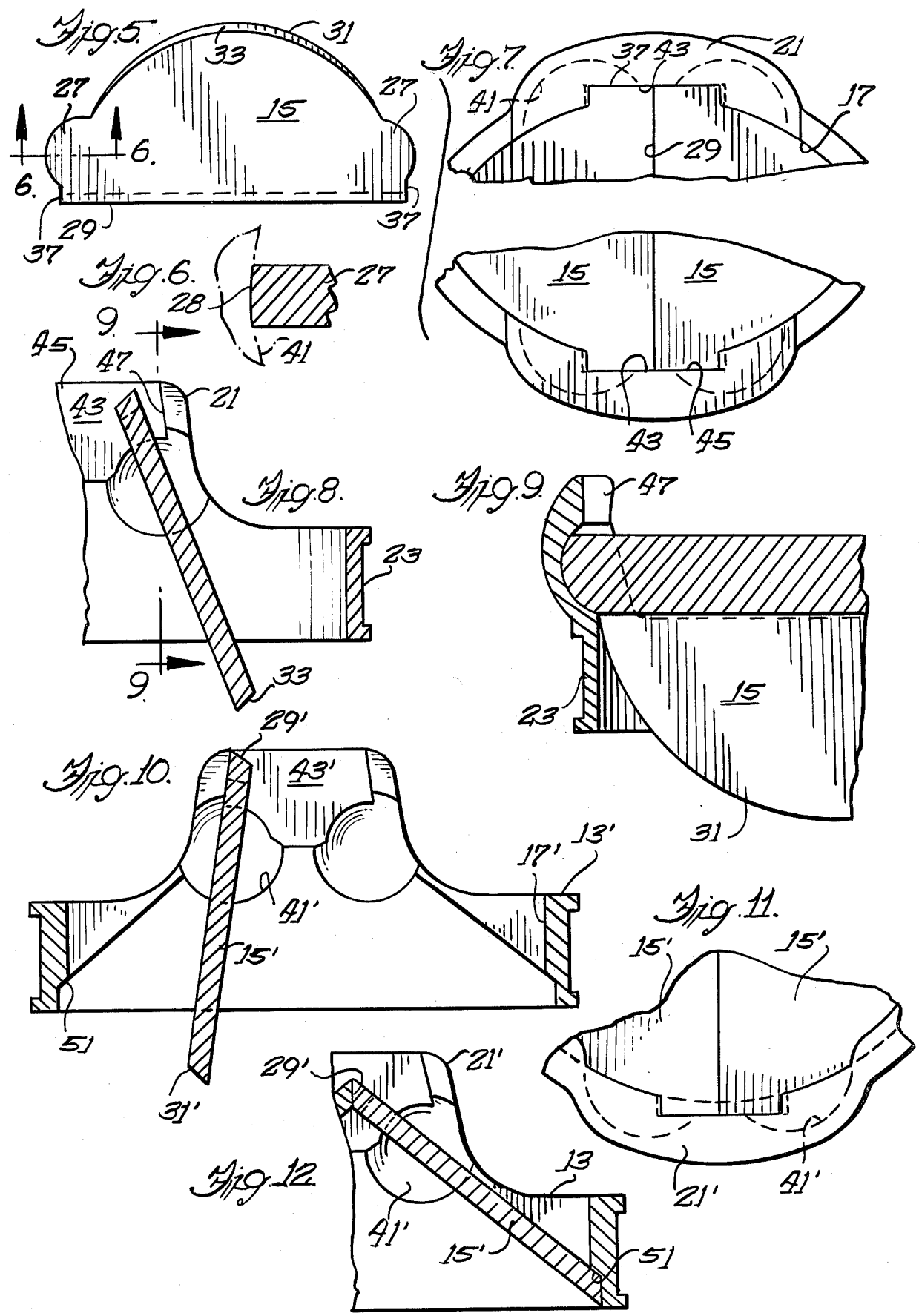

TWO-LEAFLET HEART VALVE

BACKGROUND OF THE INVENTION

This invention is related to heart valve prostheses for replacement of defective natural valves and more particularly to heart valve prostheses using pivoting valve members.

Various types of heart valve prostheses have been developed which operate hemodynamically as a result of the pumping action of the heart. Some of these valves which have been used employ a ball-and-cage arrangement, whereas others have used a disc-type arrangement for the valve member. Exemplary of a disc of the free floating type is U.S. Pat. No. 3,534,411, issued Oct. 20, 1970. Various disc-type valves having a pivotal arrangement have been developed, such as that shown in U.S. Pat. No. 3,546,711 to Bokros, issued Dec. 15, 1970, and that shown in U.S. Pat. No. 3,859,668, issued Jan. 14, 1975.

Disc-type heart valves have also been developed which use two members or leaflets, instead of a single disc, which leaflets rotate about parallel axes as a part of the opening and closing of the valve. It is the latter type of heart valve prostheses to which the present invention is directed.

SUMMARY OF THE INVENTION

The invention provides an improved version of a heart valve prosthesis which uses a pair of pivotal leaflets that have their pivotal axes defined by a pair of generally spherical edge surfaces extending in opposite directions. These spherical guides or ears are received in mating depressions formed in a pair of supports which extend upward from the annular valve body. Adjacent straight edges of the leaflets engage each other in the closed position, and stops which determine the open position of the leaflets are provided on the upstanding supports in a region outside of the depressions. As a result, the most important wear areas, namely the bearing surfaces which determine the rotational movement that occurs between the spherical ears and the mating depressions, can be designed solely to withstand the rotational movement and need not be concerned with providing the stops.

IN THE DRAWINGS

FIG. 1 is a perspective view of a heart valve embodying various features of the invention and having a pair of leaflet members which are shown in the open position;

FIG. 2 is a section view taken generally along the line 2—2 of FIG. 1;

FIG. 3 is a section view similar to FIG. 2, but showing the leaflets in the closed position;

FIG. 4 is a section view taken generally along the line 4—4 of FIG. 1;

FIG. 5 is a plan view of a leaflet from the heart valve of FIG. 1;

FIG. 6 is an enlarged sectional view taken along line 6—6 of FIG. 5 showing the bearing surface in phantom outline;

FIG. 7 is a fragmentary plan view of the valve body depicted in FIG. 3;

FIG. 8 is an enlarged fragmentary view illustrating the upstanding supports with the leaflets in a mid-way location between their open and closed positions;

FIG. 9 is a section view taken along line 9—9 of FIG. 8;

FIG. 10 is a vertical section view of a modified version of a valve body, which is very similar to that illustrated in FIGS. 1 through 4, shown with only one leaflet installed and depicted in the open position;

FIG. 11 is a fragmentary plan view of the valve body shown in FIG. 10; and

FIG. 12 is an enlarged, fragmentary, section view generally similar to FIG. 3 showing the modified heart valve of FIGS. 10 and 11 in the closed position.

DETAILED DESCRIPTION OF THE PREFERRED EMBODIMENTS

Illustrated in FIG. 1 is a heart valve 11 which has an annular valve body or housing 13 which carries a pair of pivoting leaflets or valve members 15 which open and close to control the flow of blood through a central passageway 17 in direction of the arrow 19 (FIG. 2). The leaflets 15 are supported about eccentric axes by a pair of diametrically opposed supports 21 which extend upwardly from the annular valve body 13 as depicted in FIG. 1. It should of course be understood that the valve 11 can operate in any orientation and is not significantly affected by gravity; however, for ease of explanation, the valve 11 is shown and described with the supports 21 upstanding from the annular valve body 13.

The valve body 13 is formed with a peripheral groove 23 about its exterior surface that accommodates a suturing ring (not shown) which may be any of the various type already well known in the art. The suturing ring, of course, facilitates the sewing or suturing of the heart valve 11 to the heart tissue.

The passageway 17 through the valve body 13 is preferably circular, and accordingly the internal wall surface 25 of the valve body which defines the passageway 17 preferably has the shape of a right circular cylinder. As best seen in FIG. 7, this cylindrical interior shape is carried out totally through the valve so that the facing surfaces of the supports 21 are also generally cylindrical and do not extend into the flow path of blood through the valve.

The valve body 13 and the leaflets 15 may be made of any suitable material that is biocompatible and non-thrombogenic and that will take the wear to which it will be subjected during countless openings and closings of the leaflets. Preferably, the components are made from isotropic graphite, such as that sold under the tradename POCO, which has been suitably coated with pyrolytic carbon, such as that sold under the trademark PYROLITE, which gives excellent compatibility and wear-resistance.

The leaflets 15 are generally flat and may have a uniform thickness throughout, as best seen in FIG. 2. The pivotal axis for each of the leaflets is of course eccentric to the leaflet and is defined by the location of a pair of oppositely extending ears or guides 27 which are machined or ground so that the outer edge 28 of each is that of the surface of a spheroid and preferably that of the surface of a perfect sphere. One edge 29 of the leaflet 15 is straight, and the major edge 31 is curved in a manner to match the inner surface of the passageway 17. Accordingly, the outline of the arcuate edge 31 is generally defined by a plane cutting the right cylindrical interior wall surface 25 of the valve body.

As best seen in FIG. 3, the flat surface of the leaflet, in the closed position, is at an angle A to the axis of the passageway 17. This angle should preferably be between about 60° and about 70°. The edge surface portion 33 of this arcutate portion of the leaflet 15 is machined so as to be a section of the surface of a right circular cylinder having a diameter just slightly less than the diameter of the passageway 17 so as to provide a close fit along the arcuate boundary when the leaflets 15 are in the closed position illustrated in FIG. 3. The straight-line portion 29 of the leaflet boundary has a planar edge surface 35 which is disposed at angle A to the flat upper or distal surface of the leaflet (FIG. 3).

As best seen in FIGS. 4 and 7, the length of the straight edge portion 29 of the boundary is slightly longer than the diameter of the pasageway 17, and there is a short transitional edge portion 37 (FIG. 5) which is perpendicular to the straight edge boundary 29 and extends for a short distance therefrom until it intersects the spherical surface portion 28 of the ears 27. The surface of the transitional edge portion 37 is perpendicular to the upper and lower surfaces of the leaflet. The corners at intersections of the edge 29 and the edges 37 are rounded slightly to prevent chipping.

The upstanding supports 21 contain a pair of spherical depressions 41 of a diameter slightly larger than the diameter of the spherical surface portions 28 of the ears. The material from which the valve body 13 is made has sufficient resiliency to allow the leaflets 15 to be snapped into position with the ears being received in the depressions 41. In addition, a central portion 43 of the upstanding supports 21 is machined to provide a flat vertical surface which provides clearance for the pivoting movement of the transitional edges 37 of the leaflets. Accordingly, the distance between the diametrically opposite vertical surfaces 43 is just slightly greater than the length of the straight edge boundary 29 of the leaflets.

The machining or milling to form the vertical surfaces 43 provides a vertical groove 45 within which the transitional edges of the leaflets 15 are free to move. As best seen in FIGS. 8 and 9, the side surfaces 47 of these vertical grooves are used to determine the open position of the leaflets 15. Preferably, the leaflets 15 are allowed to pivot through about 55° to about 65° of angular movement, and the side surfaces 47 of the groove are cut at angle B (FIG. 3) to the vertical plane, which angle is the difference between angle A and the amount of movement desired. Preferably, angle B, which determines the orientation of the leaflets in the open position, is between about 5° and 10°. The side surfaces 47 of the groove are planar and perpendicular to the vertical surface 43 of the groove.

One example of a heart valve 11 designed for aortic location may have an outer diameter of about 24 mm. and a central passageway 17 about 21 mm. in diameter. The length of the straight edge portion 29 of the leaflets may be about 23 mm. The radius of the spherical surface portions 28 of the ears may be about 2.4 mm., and the radius of curvature of the depressions 41 is nearly equal to that of the ears—within about 6%. In the open position, as depicted in FIG. 2, the main portions of the leaflets 15 swing downward until the transitional edge regions 37 of the distal surface contact the stops which are provided by the side surfaces 47 of the groove. During the opening movement, blood flows through the valve 11 in the direction of the arrow 19. This flow of course occurs on the pumping stroke of the heart as the respective ventricle contracts.

At the end of the stroke, the respective ventrical relaxes to draw more blood into the chamber from the atrium, and the back pressure within the left aorta causes the leaflets to swing or pivot to the closed location depicted in FIG. 3. The proportioning of the leaflets 15 is such that they pivot about the axis which is defined by the radii of the spherical surface sections of the ears 27 until the cylindrical edge surface 33 of the arcuate portion of each leaflet contacts the interior side wall 25 of the passageway, thus sealing the outer region of the passageway. As indicated above, the radius of curvature of the ears may be either slightly longer, equal to or slightly smaller than that of the depressions 41. Moreover, some slight amount of additional clearance can be provided by reducing the longitudinal distance between the ears 27. If, as is preferred, the radius of curvature of the depressions is slightly larger, the ears will move slightly within the depressions 41 until the straight-edge surface portions 35 of the two leaves contact each other, closing the central portion of the passageway to blood flow.

The heart valve is felt to contain certain improvements which provide not only good flow characteristics and ease of machinability, but also long lifetime. As best seen in FIG. 7, the central passageway 17 through the valve 11 has the shape of a right circular cylinder with no protrusions thereinto. Accordingly, this surface can be formed by a single boring or milling operation. The arrangement also provides for smooth flow of blood along the cylindrical interior surface of the wall 25.

The main wear occurs at the region where the spherical ear surfaces 28 pivot in relative movement within the spherical depressions 41 and this can be controlled by the proportioning of the radii of curvature and/or the clearance. By making the radius of the ears slightly larger, the wear region will be located near the widest part or base of the ears, as best seen in FIG. 5. Because these spherical surfaces need only define the axis of swinging or pivoting movement and because the regions of engagement in order to stop the leaflets in their precise open and closed position are separated therefrom and defined exterior of the depressions superior results are obtained relative to an arrangement where the ears 27 themselves were relied upon to determine the open and/or closed position of the leaflets.

As earlier indicated, it is the engagement of the transitional boundary portions with the side surfaces 47 of the groove that stop the leaflets in the desired open position, and the engagement of the arcuate edge surfaces 33 of the leaflets that define the closed position. By proportioning the radii of curvature within the limits of about 6% and/or adjusting the clearance, the wear can be spread over a fairly large total surface area without unduly increasing the effect of friction, and both excellent sealing of the blood passageway and wear resistance are found to result.

Although the invention has been described with regard to a particular preferred embodiment which constitutes the best mode presently known to the inventor, it should be understood that various changes and modifications as would be obvious to one having the ordinary skill in this art may be made without departing from the scope of the invention which is defined solely by the appended claims.

In this respect, should it be desired to achieve an even greater seal in the closed position along the arcuate boundary of the leaflets and to relieve somewhat the holding of narrow tolerances to achieve precise interengagement of the abutting straight edge surfaces, a ledge 51 as depicted in FIGS. 10-12, can be provided. The ledge 51 is created by machining a valve body 13' so that a central passageway 17' is provided with a slightly smaller diameter above the region wherein the arcuate boundary portion 31' of the leaflets 15' will reside. As best seen in FIGS. 10 and 11, the ledge 51 preferably terminates at the region of the depressions 41', and when such full length ledge 51 is used, the upper surface of the arcuate region of the leaflet 15' will both stop and seal tightly against the undersurface of the ledge, as depicted in FIG. 12. However, such a ledge 51 could be terminated sooner if it were primarily used as a stop instead of as a seal, by blending the ledge into the cylindrical wall, and the ledge 51 would function as an effective stop even if it only extended for a distance of about 10–15 degrees of the arcuate edge 31 of the leaflet. The relative dimensions of the radii of curvature remain the same as before mentioned.

Various of the features of the invention are set forth in the claims which follow.

What is claimed is:

1. A heart valve prosthesis including
an annular valve body having a central passageway extending therethrough,
a pair of valve leaflets,
means supporting said pair of leaflets for substantially pivotal movement between a closed position blocking blood flow through said central passageway and an open position allowing blood flow therethrough, and
stop means limiting movement of said leaflets between said open and closed positions,
wherein the improvement comprises
said leaflets each having a pair of guides projecting in opposite directions along the pivotal axis of the leaflet which are formed with spheroidal surfaces,
said annular body having a pair of upstanding supports at generally diametrically opposite locations thereon, which supports contain spheroidal depression means proportioned to receive said spheroidal guides, and
wherein said supports are formed with stops outside of said depressions which contact the distal surface of said leaflets at a region apart from said spheroidal guides and determine the open position thereof.

2. A prosthesis in accordance with claim 1
wherein the valve body wall which forms said central passageway is that of a right circular cylinder and
wherein the major peripheral arcuate edge of said each leaflet is contoured so that the surface of said edge fits flush adjacent said passageway cylindrical wall.

3. A prosthesis in accordance with claim 2
wherein a minor peripheral edge of each leaflet is straight and the edge surface thereof is planar so that the planar surfaces of said minor edges abut each other in surface-to-surface contact when said valve is in the closed position.

4. A prosthesis in accordance with claim 3 wherein said minor edge surfaces are located at an angle between about 60° and about 70° to the distal surface of said leaflets.

5. A prosthesis in accordance with any one of claims 1, 2 or 4 wherein the radius of curvature of said depression means is within about 6% of the radius of curvature of said guide surfaces.

6. A prosthesis in accordance with claim 4 wherein said stops are formed by surfaces oriented at an angle between about 5° and about 10° to the axis of said central passageway.

7. A prosthesis in accordance with claim 1 wherein said central passageway is of circular cross section throughout its entirety including the region between said supports.

8. A prosthesis in accordance with claim 1
wherein the valve body wall which forms said central passageway is that of a right circular cylinder and
wherein a tapered ledge is formed which extends into said passageway and against which ledge the distal side of a major arcuate edge portion of said leaflet abuts in the closed position.

* * * * *

UNITED STATES PATENT AND TRADEMARK OFFICE
CERTIFICATE OF CORRECTION

PATENT NO. : 4,178,639
DATED : December 18, 1979
INVENTOR(S) : Jack C. Bokros

It is certified that error appears in the above-identified patent and that said Letters Patent are hereby corrected as shown below:

In the Drawings: Sheet 1, FIGURE 2, the arrow carrying the reference numeral 19 should point in the opposite direction.

In the Abstract, line 9, "distal" should read --upstream--.

Column 2, line 31, "type" should read --types--.

Column 3, line 2, correct the spelling of "arcuate";
line 10, "distal" should read --upstream--,
line 13, correct the spelling of "passageway",
line 61, "distal" should read --upstream--.

Column 6, lines 2, 20 and 38, "distal" should read --upstream--.

Signed and Sealed this

Twenty-ninth Day of April 1980

[SEAL]

Attest:

SIDNEY A. DIAMOND

Attesting Officer  Commissioner of Patents and Trademarks